United States Patent
Vickery et al.

(10) Patent No.: US 9,095,585 B2
(45) Date of Patent: Aug. 4, 2015

(54) BIOAVAILABLE COMPOSITIONS OF AMORPHOUS PIPERIDINYL COMPOUNDS

(75) Inventors: Rodney D. Vickery, Furlong, PA (US); Kevin J. Stefanski, Burlington, NJ (US); Ching-Chiang Su, Yardley, PA (US); Michael J. Hageman, Pennington, NJ (US); Balvinder S. Vig, Milltown, NJ (US); Seema Betigeri, Hillsborough, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/233,901

(22) PCT Filed: Jul. 20, 2012

(86) PCT No.: PCT/US2012/047517
§ 371 (c)(1),
(2), (4) Date: Jan. 21, 2014

(87) PCT Pub. No.: WO2013/013114
PCT Pub. Date: Jan. 24, 2013

(65) Prior Publication Data
US 2014/0163071 A1    Jun. 12, 2014

Related U.S. Application Data

(60) Provisional application No. 61/510,160, filed on Jul. 21, 2011.

(51) Int. Cl.
*A61K 31/4465* (2006.01)
*A61K 9/14* (2006.01)
*A61K 31/445* (2006.01)

(52) U.S. Cl.
CPC ............ *A61K 31/4465* (2013.01); *A61K 9/146* (2013.01); *A61K 31/445* (2013.01)

(58) Field of Classification Search
None
See application file for complete search history.

(56) References Cited

U.S. PATENT DOCUMENTS

| 8,299,098 B2 | 10/2012 | Santella | |
|---|---|---|---|
| 2004/0156905 A1 * | 8/2004 | Babcock et al. | 424/486 |
| 2009/0326010 A1 * | 12/2009 | Santella | 514/327 |
| 2010/0261768 A1 * | 10/2010 | Hartley et al. | 514/364 |

FOREIGN PATENT DOCUMENTS

WO    WO 2014/042945    3/2014

OTHER PUBLICATIONS

Newman (Basics of Amorphous and Amorphous Solid Dispersion, PPXRD Pharmaceutical Powder X-ray Diffraction Symposium presentation, 2010, pp. 1-55).*
Hynes et al. (Discovery of the CCR1 Antagonist, BMS-817399, for the Treatment of Rheumatoid Arthritis, J. Med. Chem., 2014, vol. 57, pp. 7550-7564).*
Gamble, J.F. et al., "Application of imaging based tools for the characterisation of hollow spray dried amorphous dispersion particles", International Journal of Pharmaceutics, vol. 465, pp. 210-217 (2014).
Karavas, E. et al., "Effect of hydrogen bonding interactions on the release mechanism of felodipine from nanodispersions with polyvinylpyrrolidone", European Journal of Pharmaceutics and Biopharmaceutics, vol. 63, pp. 103-114 (2006).
Paudel, A. et al., "Manufacturing of solid dispersions of poorly water soluble drugs by spray drying: Formulation and process considerations", International Journal of Pharmaceutics, vol. 453, pp. 253-284 (2013).
Vo, C.L. et al., "Current trends and future perspectives of solid dispersions containing poorly water-soluble drugs", European Journal of Pharmaceutics and Biopharmaceutics, vol. 85, pp. 799-813 (2013).

* cited by examiner

*Primary Examiner* — Bethany Barham
*Assistant Examiner* — Ping Cao
(74) *Attorney, Agent, or Firm* — Hong Liu (57) ABSTRACT

This invention relates to solid amorphous dispersions comprising Compound I having the formula (formula I), or stereoisomers thereof, and one or more polymers. More particularly, this invention relates to bioavailable amorphous solid dispersions of Compound I that are unexpectedly stable in suspension and in the solid state for extended periods of time that may be used for tabletting.

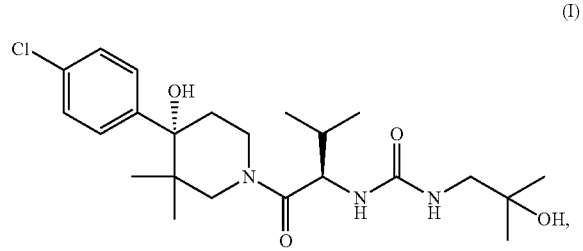

14 Claims, 5 Drawing Sheets

FIG. 1

Optical Microscopy of Crystalline Compound I

Bright Field: Needle Shaped Crystals

Crossed Polarized: Birefringence Observed

FIG. 2

Optical microscopy of amorphous spray dried Compound I with PVP K30, in a 10:1 (w/w%) ratio Bright Field: Sphere shaped particles Crossed Polarized: No birefringence observed

FIG. 3

Powder X-Ray Diffraction of Crystalline Compound I vs. Amorphous Spray Dried Compound I:PVP K30, 10:1 (w/w%)

BIOAVAILABLE COMPOSITIONS OF AMORPHOUS PIPERIDINYL COMPOUNDS

FIELD OF THE INVENTION

This invention relates to pharmaceutical formulations containing a piperidinyl modulator of chemokine receptor activity and one or more polymers. More particularly, this invention relates to bioavailable amorphous solid dispersions of the piperidinyl modulator that are stable in suspension and in the solid state for extended periods of time containing the piperidinyl modulator together with one or more pharmaceutically acceptable polymers.

BACKGROUND OF THE INVENTION

Chemokines are chemotactic cytokines, of molecular weight 6-15 kDa, that are released by a wide variety of cells to attract and activate, among other cell types, monocytes, macrophages, T and B lymphocytes, eosinophils, basophils and neutrophils. The chemokines and their cognate receptors have been implicated as being important mediators of inflammatory, infectious, and immunoregulatory disorders and diseases, including asthma and allergic diseases, as well as autoimmune pathologies such as rheumatoid arthritis and arthrosclerosis (reviewed in: Carter, P. H., *Current Opinion in Chemical Biology*, 6:510 (2002); Trivedi et al., *Ann. Reports Med. Chem.*, 35:191 (2000); Saunders et al., *Drug Disc. Today*, 4:80 (1999); Premack et al., *Nature Medicine*, 2:1174 (1996)). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-1α binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MIP-1α, experienced a rapid and significant influx of leukocytes to the site of injection (Brummet, M. E., *J. Immun.*, 164:3392-3401 (2000)).

It is known that MIP-1α is elevated in the synovial fluid and blood of patients with rheumatoid arthritis. Moreover, several studies have demonstrated the potential therapeutic value of antagonism of the MIP-1α/CCR1 interaction in treating rheumatoid arthritis.

It should also be noted that CCR-1 is also the receptor for the chemokines RANTES, MCP-3, HCC-1, Lkn-1/HCC-2, HCC-4, and MPTP-1 (Carter, P. H., *Curr. Opin. Chem. Bio.*, 6:510-525 (2002)).

Recently, inhibitors of CCR-1 that may be useful in the treatment of inflammatory disorders have been discovered. In particular, Compound I of the formula is disclosed in US 2009/0326010 A1 (assigned to Applicant) which published on Dec. 31, 2009. This compound is highly crystalline, non-ionizable in a pH range of 2-11, and has low aqueous solubility at room temperature. Suspensions of compound I, including nanosuspensions, have demonstrated unacceptable bioavailabilities in rats.

Solid dispersion systems of amorphous drug have been investigated with the objective of inhibiting crystal growth and enhancing the dissolution of poorly water soluble drugs. See, e.g., *European Journal of Pharmaceutics and Biopharmaceutics*, 63:103-114 (2006). Generally, it has been found that effective solid amorphous dispersions require the incorporation of at least 20% w/w or higher of polymers (see e.g., WO 10/102,245 A and US 2003/0219489). In one instance it was reported that 5% w/w of PVP may inhibit the crystal growth of indomethacin in a molecular dispersion, reportedly via hydrogen bonding of the active ingredient with the PVP polymer. See *Pharmaceutical Research*, 16:1722-1728 (1999). Also, polymer formulations of antihelmintics have been disclosed that exhibit increased solubility and anthelmintic activity. See EP 0 224 249.

What is therefore now needed in the art is one or more bioavailable amorphous formulations of Compound I that are stable, have a desirable pharmaceutical profile, and are amenable to manufacturing conditions.

SUMMARY OF THE INVENTION

Accordingly, the present invention provides an amorphous solid dispersion comprising Compound I of the formula or a stereoisomer or pharmaceutically acceptable salt form thereof and a polymer,
wherein said polymer is selected from the group consisting of polyvinylpyrrolidone (PVP), polyvinylpyrrolidone-vinyl acetate copolymer (PVP-VA), hydroxypropylmethylcellulose-acetate succinate copolymer (HPMC-AS) and hydroxypropylmethylcellulose (HPMC).

Methods of preparing the compositions of the invention are also provided.

The invention also provides pharmaceutical compositions comprising a pharmaceutically acceptable carrier and a therapeutically effective amount of the amorphous solid dispersion of the present invention.

Also provided herein is a pharmaceutical tablet containing the amorphous solid dispersion comprising Compound I and one or more pharmaceutically acceptable excipients.

A method for the treatment and prevention of osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, neuropathic pain, inflammatory bowel disease, alveolitis, ulcerative colitis, systemic lupus erythematosus, nephrotoxic serum nephritis, glomerulonephritis, asthma, multiple sclerosis, arthrosclerosis, rheumatoid arthritis, restenosis, organ transplantation, psoriatic arthritis, multiple myeloma, allergies, for example, skin and mast cell degranulation in eye conjunctiva, hepatocellular carcinoma, colorectal cancer, osteoporosis, renal fibrosis, and other cancers, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis comprising a therapeutically effect amount of an amorphous solid dispersion of Compound and one or more pharmaceutically effective excipients.

More particularly, there is provided herein a method for the treatment and prevention of inflammatory diseases, allergic and autoimmune diseases, including, without limitation, rheumatoid arthritis and transplant rejection, which comprises administering to a patient a therapeutically effective amount of the amorphous solid dispersion comprising Compound I and one or more pharmaceutically acceptable excipients.

The present invention is directed to these, as well as other important ends, hereinafter described.

DETAILED DESCRIPTION OF THE INVENTION

The present invention provides amorphous solid dispersions of Compound I that have an unexpectedly advantageous pharmaceutical profile. The dispersions of the present invention exhibit superior oral bioavailability and are surprisingly stable both in suspension and in the solid state.

In one embodiment, the present invention comprises an amorphous solid dispersion composition of Compound I of the formula or stereoisomers thereof, wherein the polymer used is selected from the group consisting of PVP, PVP-vinyl acetate copolymer, HPMC-AS and HPMC, particularly PVP and HPMC-AS, and more particularly PVP.

In another embodiment there is provided the dispersion wherein the w/w % of Compound I to polymer is in the range of from about 99 to about 80% Compound I and from about 1 to about 20% polymer.

In a further embodiment, there is provided the dispersion wherein the w/w % of Compound I to polymer is in the range of from about 95 to about 85% Compound I and from about 5 to about 15% polymer.

In another embodiment, the w/w % of Compound I to polymer is in the range of from about 93 to about 88% Compound I and from about 7 to about 12% polymer.

In yet another embodiment, the dispersion is prepared by hot-melt extrusion, lyophilization, or spray-drying methods, particularly by spray-drying.

In another embodiment, a dispersion is provided that is stable in suspension for at least about 5 days.

In a further embodiment the dispersion exhibits less than about 5% crystallization when stored at 25° C./60% RH for at least 2 years.

In yet another embodiment Compound I contained within the dispersion exhibits less than about 3% degradation when stored at 25° C./60% RH for at least two years.

A pharmaceutical composition comprised of a pharmaceutically acceptable carrier and a therapeutically effective amount of the dispersion.

Another embodiment provides an orally bioavailable composition comprising the dispersion.

In a further embodiment the composition is tabletted.

A preferred tabletted embodiment comprises the dispersion of the present invention in a weight range of 10-75%, preferably 20-60%, and most preferably 45-55%.

A preferred tabletted embodiment comprises one or more fillers, for example lactose and/or microcrystalline cellulose, in a total weight percent range of 10-86%, more preferably 23-76%, and most preferably 35-68%.

A preferred tabletted embodiment comprises a disintegrant in a weight percentage of 4-10%, preferably 4-9%, and more preferably 5-7%.

A preferred tabletted embodiment comprises one or more flow-aids, for example CAB-O-SIL® M-5P, in a total weight percent range of 0.1-3%, and preferably 0.25-2%.

A preferred tabletted embodiment comprises a lubricant, for example magnesium stearate, in a weight percent range of 0.25-2.0%, preferably 0.25-1.0%, and more preferably 0.25-0.75%.

A more preferred tabletted embodiment comprises (in weight percent ranges): 27-55% of the dispersion of the present invention, 35-68% of one or more fillers, 5-7% of a disintegrant, 0.25-2.0% one or more flow-aids, and 0.25-0.75% of a lubricant.

In a further embodiment the composition is prepared in capsule form.

In another embodiment, the present invention is directed to i) a method for treating disorders, comprising administering to a patient in need thereof a therapeutically effective amount of an amorphous solid dispersion formulation containing compound (I); ii) use of an amorphous solid dispersion of Compound I for use in treating a disorder; or iii) use of an amorphous solid dispersion formulation of Compound I in the preparation of a medicament for the treatment of a disorder, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, neuropathic pain, inflammatory bowel disease, alveolitis, ulcerative colitis, systemic lupus erythematosus, nephrotoxic serum nephritis, glomerulonephritis, asthma, multiple sclerosis, arthrosclerosis, rheumatoid arthritis, restenosis, organ transplantation, psoriatic arthritis, multiple myeloma, allergies, for example, skin and mast cell degranulation in eye conjunctiva, hepatocellular carcinoma, colorectal cancer, osteoporosis, renal fibrosis, and other cancers, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In a further embodiment, the present invention is directed to i) a method for treating inflammatory diseases, comprising administering to a patient in need thereof a therapeutically effective amount of an amorphous solid dispersion formulation containing Compound (I); ii) use of an amorphous solid dispersion of Compound I for use in treating inflammatory diseases; or iii) use of an amorphous solid dispersion formulation of Compound I in the preparation of a medicament for the treatment of a inflammatory disease comprising administering to a patient in need thereof a therapeutically effective amount of an amorphous solid dispersion formulation containing compound (I).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Figure 1:
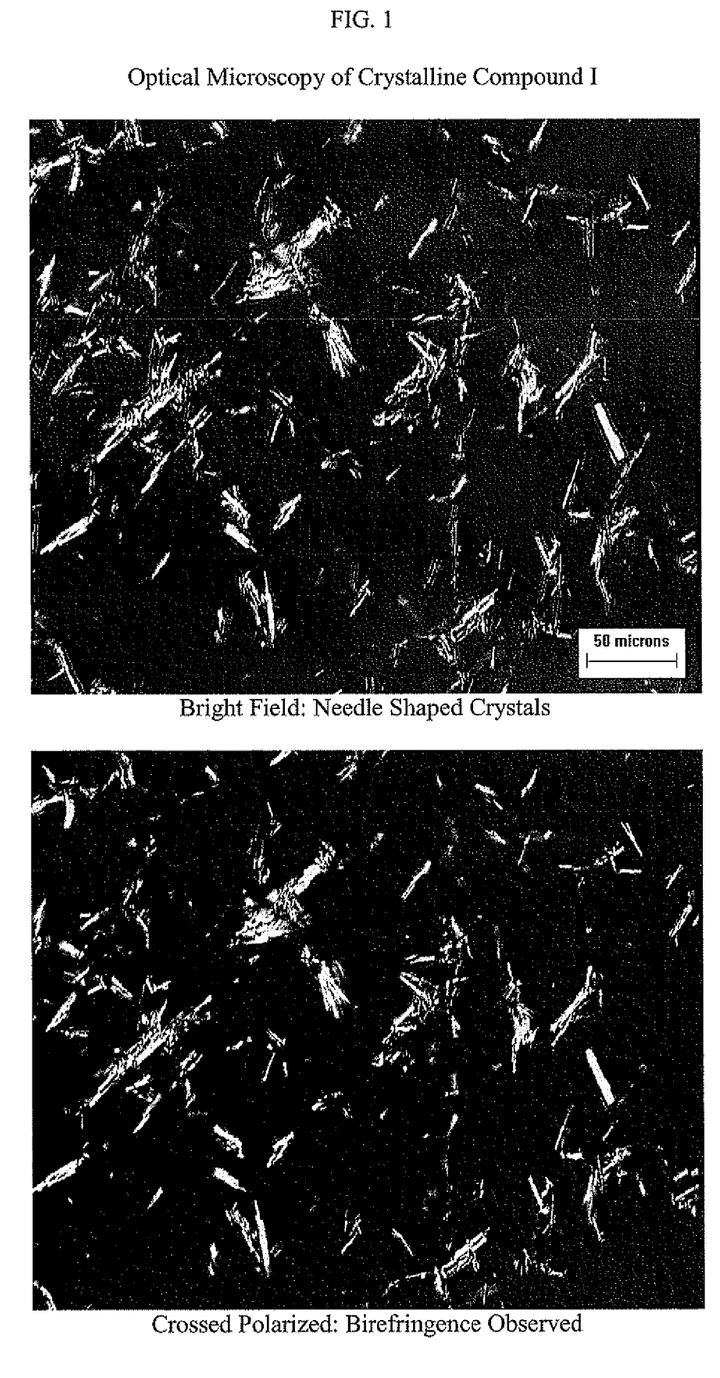
FIG. 1: Optical microscopy of crystalline Compound I.
Figure 2:
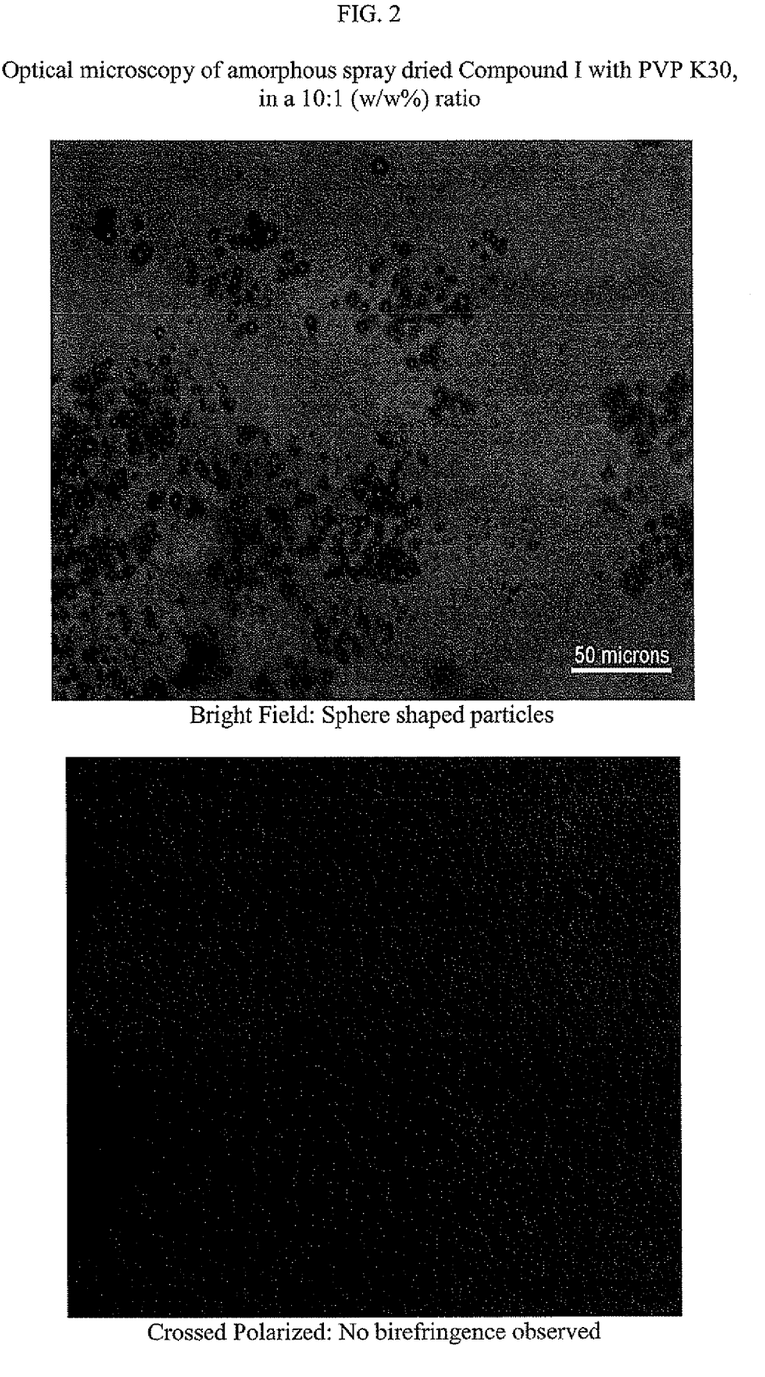
FIG. 2: Optical microscopy of amorphous spray dried Compound I with PVP K30, in a 10:1 (w/w %) ratio.
Figure 3:
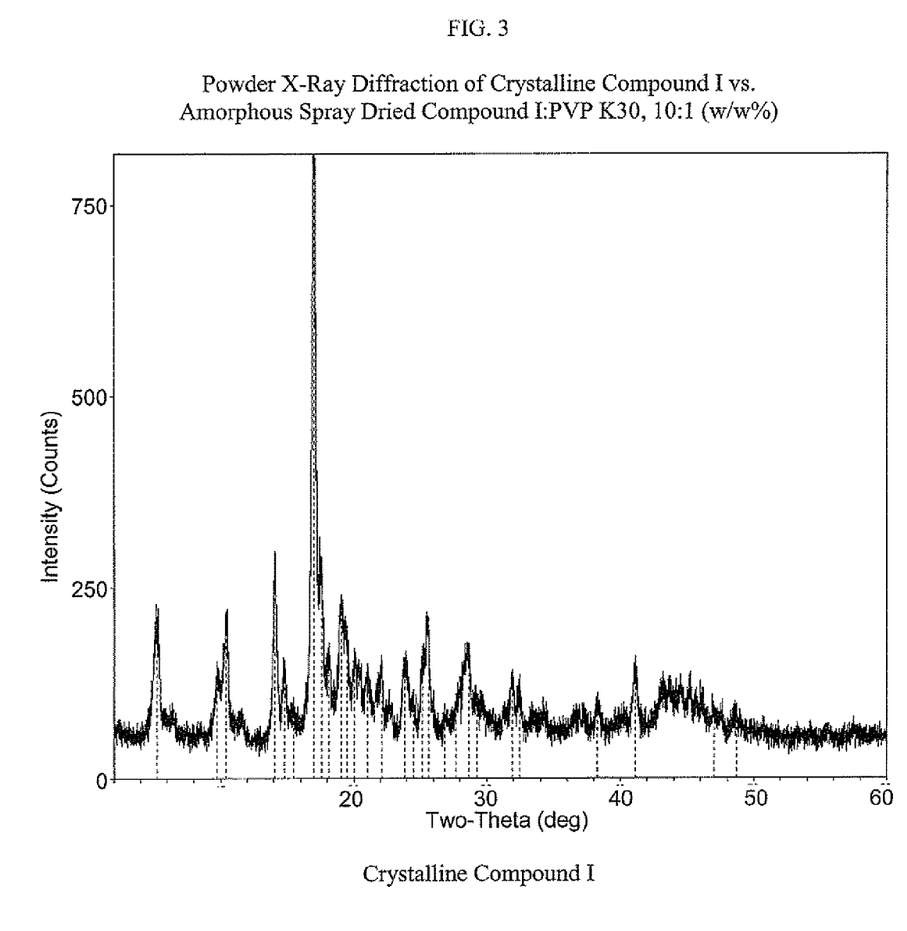
FIG. 3: Powder X-Ray diffraction of crystalline Compound I vs. amorphous spray dried Compound I:PVP K30, 10:1 (w/w %).

In order to prepare the compositions herein above described, various preparation means available to the skilled artisan may be utilized. The amorphous dispersions of the present invention may be prepared by hot-melt extrusion, lyophilization, or spray-drying. In order to prepare the compositions described herein it is preferred to utilize spray drying procedures available in the art. Preferred spray drying reaction conditions comprise the use of acetone, methanol, or ethanol solutions (2-40 w/v%) with an inlet temperature of the spray dry apparatus of typically about 70-175° C. Typically, the spray-dried material has particle size wherein 90% of the particles are under 50 µm. FIGS. 1-3 confirm the non-crystalline, amorphous nature of the present invention. The dispersions of this invention are surprisingly stable, as illustrated in Example 2.

In particular, aqueous suspensions of these dispersions are unexpectedly stable as optical microscopy confirms that no crystallization occurs in suspensions of the dispersions, even after 8 days at room temperature (see Example 2). Also, the dispersions of the present invention are chemically and physically stable. For example based on the data given in Example 2, it is expected that Compound I contained within the dispersion exhibits less than 3% degradation when stored at 25° C./60% RH for at least 2 years. In addition, the dispersions are expected to exhibit less than about 5% crystallization when stored at 25° C./60% RH for at least 2 years.

The compositions of the invention herein described according to the various embodiments may then be tabletted using equipment and procedures available in the art.

Furthermore, when desired or necessary, suitable additional binders, lubricants, disintegrating agents, and coloring agents can also be incorporated into the tabletting mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, magnesium stearate, and the like.

Disintearants include, without limitation, starch, methylcellulose, agar, bentonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, alginate, gelatin, or polyvinylpyrrolidone, a solution retardant such as paraffin, a resorption accelerator such as a quaternary salt and/or and absorption agent such as bentonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

By way of non-limiting example, tablets containing about 1 to about 1000 mg, preferably about 50 to about 600 mg and preferably about 100 to about 500 mg of Compound I may be made using the compositions herein described. Other dosage units are within the scope of the invention hereof. In particular, tablets containing spray-dried composition containing Compound I and a polymer, including PVP and HPMC-AS have shown improved in vitro dissolution rates, good in vivo oral bioavailability in dogs, and good chemical/physical stability.

Further, a method of inhibiting CCR1 activity in a patient comprises administering to the patient a therapeutically effective amount of a pharmaceutical tablet according to one or more of the embodiments herein above described. The term "therapeutically effective amount" means the total amount of the active component of the method that is sufficient to show a patient benefit, i.e., symptomatic or disease modifying treatment. When applied to an individual active ingredient, administered alone, the term refers to that ingredient alone. When applied to a combination, the term refers to combined amounts of the active ingredients that result in the therapeutic effect, whether administered in combination, serially or simultaneously.

This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

Definitions

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th Edition, p. 1418, Mack Publishing Company, Easton, Pa. (1985), the disclosure of which is hereby incorporated by reference. Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

The synthesis of Compound I may be prepared as described in patent application US 2009/0326010 A1 assigned to the Applicant which published on Dec. 31, 2009 in reaction schemes, descriptions and examples thereof, as well by relevant literature procedures that are known to one skilled in the art.

EXAMPLES

Example 1

Crystallization Inhibition

Figure 4:
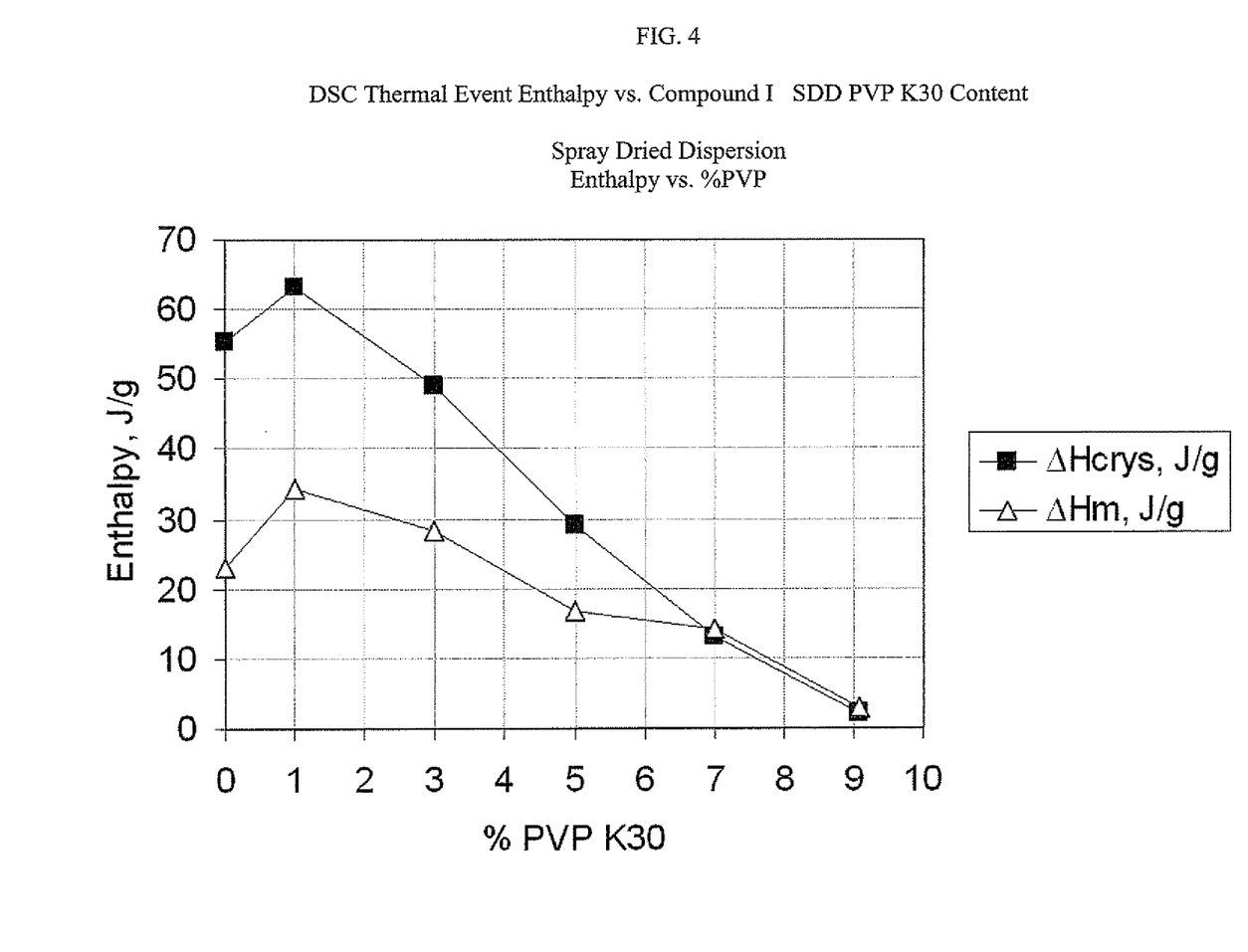
FIG. 4: DSC thermal event enthalpy vs. spray-dried dispersion ("SDD") of Compound I and PVP K30 content.

Amorphous spray dried dispersions of Compound I ("SDDs") have been prepared with PVP K30 concentrations ranging from 0 to 50%. A summary of the characterization results is included in Table 1. The plots of the enthalpy of crystallization exotherm and the enthalpy of the final melting/decomposition endotherm observed during DSC analysis vs. the SDD PVP K30 content converge at 7% PVP K30 (FIG. 4). Based on the DSC results, the optimal PVP K30 concentration range for crystallization inhibition in the solid-state ranges between about 5 to about 15%.

TABLE 1

TGA and DSC results for SDDs with 0-50% PVP K30

| % PVP K30 | TGA % wt. loss at 175° C. | Tg, ° C. | ΔH crys., J/g | ΔHm, J/g reversible |
|---|---|---|---|---|
| 0 | 0.55 | 119.1 | 55.4 (175° C.) | 23.0 (201° C.) |
| 1 | 0.53 | 118.8 | 63.3 (173° C.) | 34.4 (203° C.) |
| 3 | 0.62 | 120.6 | 49.0 (178° C.) | 28.2 (201° C.) |
| 5 | 0.61 | 120.3 | 29.0 (185° C.) | 16.9 (198° C.) |
| 7 | 0.42 | 121.6 | 13.2 (187° C.) | 14.1 (199° C.) |
| 9 | 0.75 | 124.2 | 2.2 (181° C.) | 2.9 (199° C.) |
| 15 | 0.80 | 125.9 | No exotherm | No endotherm |
| 20 | 0.97 | 128.3 | No exotherm | No endotherm |
| 30 | 1.23 | 134.0 | No exotherm | No endotherm |
| 50 | 2.00 | 141.8 | No exotherm | No endotherm |

Example 2

Stability

The performance of the SDDs was evaluated in a suspension formulation physical stability study. After 8 days at room temperature the suspension formulation of the SDDs with relatively higher Tg's were observed to be more physically stable as an amorphous form, with about 5% PVP being the observed transition concentration in regards to physical stability in the suspension formulation. (Table 2).

TABLE 2

Physical Stability of 10 mg/mL Suspensions of SDDs in 0.25% HPMC E4M

| % PVP K30 (Tg) | 10 mg/mL SDD Suspension in 0.25% HPMC E4M Optical Microscopy Observation Time at Room Temperature | | | |
|---|---|---|---|---|
| | 1 Day | 5 Days | 8 Days | 14 Days |
| 0 (Tg = 119.1° C.) | Amorphous | Trace crystallization | Significant crystallization | Significant crystallization |
| 1 (Tg = 118.8° C.) | Amorphous | Amorphous | Some crystallization | Significant crystallization |
| 3 (Tg = 120.6° C.) | Amorphous | Amorphous | Some crystallization | Significant crystallization |
| 5 (Tg = 120.3° C.) | Amorphous | Amorphous | Amorphous | Significant crystallization |
| 7 (Tg = 121.6° C.) | Amorphous | Amorphous | Amorphous | Significant crystallization |
| 9 (Tg = 124.2° C.) | Amorphous | Amorphous | Amorphous | Significant crystallization |

The suspension physical stability results confirm that the optimal PVP K30 concentration range for crystallization inhibition of SDDs in the suspension formulation is greater than 5 w/w %.

The physical stability of SDDs containing 9 to 50% PVP K30 was also evaluated. The TGA and DSC Tg results for the SDDs are summarized in Table 1. The hygroscopicity profiles (VTI method) are summarized in Table 3. The TGA weight loss and Tg values after storage at 40° C./75% RH (open vial) for 4 weeks for the Compound I SDD's with 9-50% PVP K30 are listed in Table 4.

A 6 month stability study was carried out at 5° C. and 25° C./60% RH to assess the chemical and physical stability of the SDD containing 9% PVP K30. The potency and purity data are summarized in Table 5. No significant change in potency and purity were measured. Furthermore, no crystalline peaks were detected by XRD. Based on these data, the SDD is expected to be stable (i.e., exhibit less than 5% crystallinity and less than 3% chemical degradation) for at least 2 years.

The physical stability of the SDDs was also assessed by isothermal microcalorimetry (TAM) experiments. Based on this data, TAM confirmed that the time to 5% crystallization when stored at 25° C./60% RH for an SDD containing 9% PVP K30 should be at least 2 years.

TABLE 3

VTI results for SDDs with 9-50% PVP K30

| % PVP K30 | Weight gain at 90% RH |
|---|---|
| 9 | 7.3 |
| 15 | 7.1 |
| 20 | 8.9 |
| 30 | 11.9 |
| 50 | 23.6 |

TABLE 4

Physical Stability of SDD's Manufactured With 9 to 50% PVP K30

| % PVP K30 | TGA % Weight Loss at 175° C. | | Tg, ° C. | | |
|---|---|---|---|---|---|
| | Time Zero | 4 Weeks 40° C./ 75% RH | Time Zero Vented Pan | Time Zero Hermetic Pan | 4 Weeks 40° C./75% RH Hermetic Pan |
| 9 | 0.75 | 2.96 | 124.2 | 104.7 | — |
| 15 | 0.80 | 3.31 | 125.9 | 115.0 | 82.1 |
| 20 | 0.97 | 3.67 | 128.3 | 116.1 | 81.1 |
| 30 | 1.23 | 4.87 | 134.0 | 118.1 | 79.8 |
| 50 | 2.00 | 8.13 | 141.8 | 122.5 | 66.5 |

TABLE 5

Chemical Stability of SDD Containing 9% PVP K30

| Conditions | Time | Potency (% of Label) | Purity (%) of Compound I in SDD |
|---|---|---|---|
| Initial | Initial | 101.2 | 99.9 |
| 5° C. | 1 month | 98.1 | 99.8 |
| 25° C./60% RH | 1 month | 101.5 | 99.9 |
| 5° C. | 3 month | 100.8 | 99.9 |
| 25° C./60% RH | 3 month | 98.5 | 99.9 |
| 5° C. | 6 month | 101.8 | 99.9 |
| 25° C./60% RH | 6 month | 100.3 | 99.9 |

100% Label = 91% Compound 1

Example 3

Bioavailability

In a formulation comparison study, four types of spray dried formulations were prepared: 1) spray dried Compound I without polymer; 2) spray dried Compound I: HPMC AS-LG 1:2 (w/w %); 3) spray dried Compound I: HPMC AS-MG 1:2 (w/w %); and 4) spray dried Compound I:PVP K30 10:1 (w/w %). Upon administration in rats at a dose of 10 mg/kg, the suspension of a spray dried solid dispersion formulation of amorphous Compound I: PVP K30, 10:1 (w/w %) in a 0.25% HPMC E4M/25 mM citrate pH 3 vehicle achieved a bioavailability of 100%. In comparison, the achieved bioavailability was 51% from dosing the suspension from the spray dried Compound without polymer, 23% from spray dried Compound I: HPMC AS-LG 1:2 (w/w %), and 47% from spray dried Compound I: HPMC AS-MG 1:2 (w/w %).

Example 4

Tabletting

A tablet was prepared by direct compression with the components listed in the following Tablet. The spray dried 91% Compound I:PVP K30 component and all excipients except the lubricant were passed through a screen, then blended in a mixer. The lubricant was then passed through a screen into the mix and blended further. The final blend was then compressed into tablets with a tabletting machine.

TABLE 6

Tablet Formulation

| Component | Amount (% of total) | (mg/tablet) |
|---|---|---|
| 91% Compound I:PVP K30 | 54.95 | 274.75 |
| Disintegrant (e.g., Ac-Di-Sol) | 6.00 | 30.00 |
| Brittle filler (e.g., Fastflow lactose) | 19.15 | 95.75 |
| Ductile filler (e.g., AVICEL ® PH 200) | 19.15 | 95/75 |
| Flow-aid (e.g., Cab-Sil M5P) | 0.50 | 2.50 |
| Lubricant (e.g., magnesium stearate) | 0.25 | 1.25 |
| Total | 100 | 500 |

While the invention has been described in detail and with reference to specific embodiments thereof, it will be apparent to one skilled in the art that various changes and modifications can be made therein without departing from the spirit and scope thereof.

What is claimed is:

1. An amorphous solid dispersion comprises compound (I) of the formula or a stereoisomer thereof and a polymer, wherein the polymer is selected from the group consisting of polyvinylpyrrolidone (PVP), polyvinylpyrrolidone-vinyl acetate copolymer (PVP-VA), hydroxypropylmethylcellulose-acetate succinate copolymer (HPMC-AS) and hydroxypropylmethylcellulose (HPMC).

2. The amorphous solid dispersion according to claim 1 wherein the weight ratio of compound I to the polymer is in the range of from about 4:1 to 99:1.

3. The amorphous solid dispersion according to claim 2 wherein the weight ratio of compound I to the polymer is in the range of from about 5.67:1 to 19:1.

4. The dispersion according to claim 3 wherein the weight ratio of compound I to the polymer is in the range of from about 7.3:1 to 13.3:1.

5. The amorphous solid dispersion according to claim 1 is prepared by hot-melt extrusion, lyophilization or spray-drying.

6. The amorphous solid dispersion according to claim 5 is prepared by spray-drying.

7. The amorphous solid dispersion of claim 1, wherein said dispersion exhibits less than about 5% crystallization when stored at 25° C/60% RH for at least 2 years.

8. The amorphous solid dispersion of claim 1, wherein said dispersion exhibits less than about 3% degradation of Compound I when stored at 25° C/60% RH for at least two years.

9. The amorphous solid dispersion according to claim 1 wherein the polymer is polyvinylpyrrolidone (PVP).

10. The amorphous solid dispersion according to claim 1 wherein the polymer is hydroxypropylmethylcellulose-acetate succinate copolymer (HPMC-AS).

11. A pharmaceutical composition comprises a pharmaceutically acceptable carrier and a therapeutically effective amount of the amorphous solid dispersion according to claim 1.

12. The composition of claim 11, wherein said composition is tabletted.

13. The composition of claim 11, wherein said composition is prepared in a capsule form.

14. A method for treating a disorder comprising administering to a patient in need thereof a therapeutically effective amount of the amorphous solid dispersion according to claim 1; wherein said disorder is rheumatoid arthritis.

* * * * *